United States Patent [19]

Latzke

[11] Patent Number: 4,489,711
[45] Date of Patent: Dec. 25, 1984

[54] MAGNETIC PLASTER

[75] Inventor: Arno W. Latzke, Wolfhalden, Switzerland

[73] Assignee: Energy-Pak, Ltd., Switzerland

[21] Appl. No.: 353,056

[22] Filed: Mar. 1, 1982

[30] Foreign Application Priority Data

Oct. 2, 1981 [DE] Fed. Rep. of Germany ....... 3139280
Dec. 3, 1981 [DE] Fed. Rep. of Germany ....... 3147852

[51] Int. Cl.³ .............................................. A61N 1/40
[52] U.S. Cl. ................................................. 128/1.3
[58] Field of Search ................................. 128/1.3–1.5; 335/303

[56] References Cited

U.S. PATENT DOCUMENTS 3,483,494 12/1969 Cromie .................................. 335/303
3,546,643 12/1970 Virostek .............................. 335/303

FOREIGN PATENT DOCUMENTS 3600 of 1872 United Kingdom ................. 128/1.3

OTHER PUBLICATIONS

Hartwig, R. "Device for Generating an Magnetic Field at Parts of the Body", German Gebrauchmuster-Anmeldung (Utility Model Application No. 6904160, Feb. 1, 1969.

Primary Examiner—Kyle L. Howell
Assistant Examiner—Francis J. Jaworski
Attorney, Agent, or Firm—Marshall, O'Toole, Gerstein, Murray & Bicknell

[57] ABSTRACT

Magnetic plasters are prepared from elastic magnetizable plastics sheets, which are either self-adhesive or may be fixed by means of self-adhesive plasters. They may optionally contain substances which stimulate the circulation of the blood in the self-adhesive layer.

15 Claims, 4 Drawing Figures

MAGNETIC PLASTER

The present invention relates to magnetic plasters for therapeutical use, more specifically for the magnetic therapy of rheumatism, arthralgia, sciatica, lumbago and other diseases which may successfully be treated by means of magnetic fields.

There has been known to employ expensive equipment in the magnetic therapy, but also to apply therapeutical magnetic plasters consisting of a ferrite wafer and a self-adhesive sticking plaster. Such magnetic therapeutical plasters have been known, for example, from the German Utility Model No. 79 19 808. The drawback of said known therapeutical magnetic plasters is that they will only be effective when they are sticked to the proper locations. Finding the correct points of attachment is especially difficult for the layman, but as well for a physical therapist or physician having less routine in such treatments. There has now been found, that the rate of success in applying the previously known therapeutical magnetic plasters could still be enhanced if the ferrite wafers would be attached at the optimum places each.

It is one object of the present invention to improve the known magnetic therapy and, hence, to increase the rate of success thereof and to simplify the handling. It is another object of the present invention to develop new applications of the magnetic therapy.

DESCRIPTION OF THE PREFERRED EMBODIMENTS

Figure 1:
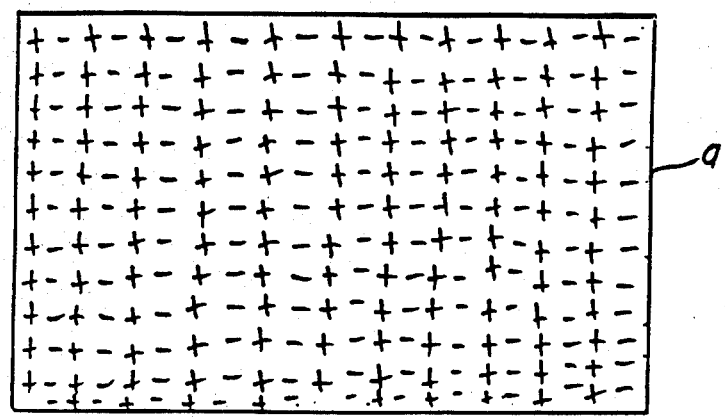
FIG. 1 shows a top plan view of a self-adhesive rubber sheet with alternating strips of (+) poles and (−) poles.

Surprisingly, said problems are solved by a magnetic plaster consisting of a flexible, permanently magnetizable and magnetized plastic sheet, which has a thickness of from 0.2 to 5 mm and is compatible with the skin, which sheet is self-adhesive or may be attached to the skin by means of a self-adhesive plaster compatible with skin.

In order to avoid too strong perspiration at those locations of the body which are susceptible to increased transpiring, and to enable the moisture to vent, it is recommendable to perforate or to slit the plaster according to the invention. As a matter of experience, holes having a diameter of from 1 to 3 mm, arranged at mutual distances of from 3 to 40 mm, will suffice for constituting such perforation. The distances may, however, basically be chosen between 2 and 100 mm, and the diameters may, as well, be from 1 to 50 mm. The slits should have a length of from 8 to 40 mm, be at mutual distances of from 8 to 40 mm, and preferably arranged in staggered positions to each other. The slits may, however, have a length of from 2 to 100 mm and be present with mutual distances of from 2 to 100 mm.

The magnetic plasters according to the present invention may have any form, while they are preferred to have circular, oval, square or rectangular shape. It may be recommendable to round the corners of square or rectangular forms in order to avoid irritations of the skin. The magnetic plasters according to the invention are not limited as to the size thereof, while length and width should, however, be in the range from 5 to 1000 mm, preferably from 5 to 250 mm. Smaller plasters than those having a diameter of 5 mm are hardly of any advantage over conventional therapeutical magnetic plasters with ferrite wafers. Larger dimensions may result in difficulties when the plasters are to be attached to those parts of the body to be treated. A preferred embodiment of the magnetic plaster according to the invention is rectangular with rounded corners and has dimensions of 60×100 mm. Plasters having the form of strips are preferred for certain applications.

It is, however, bascially as well possible to cut magnetic plasters according to the invention in larger pieces which can be used to wrap the patient for a limited period of time. To this end it may possibly make sense to preheat the magnetic plasters according to the invention, in order to enhance the heat generation by the magnetic fields by the heat supplied from outside.

As the flexible, permanently magnetizable and magnetized plastic sheet, which is compatible with the skin, for the magnetic plaster according to the invention, any sufficiently flexible inert plastic sheets, which are, above all, compatible with the skin and contain magnetizable particles, e.g. of ferrite or chromium dioxide, may be used. Rubber-elastic plastic sheets made from natural or synthetic rubbers or from silicone rubber are particularly preferred. These sheets are permanently magnetized by means of strong magnetic fields. By this process magnetic poles are formed at the side of the plastic sheet which faces the skin. While it is basically possible to so permanently magnetize the sheet that, surface which faces the skin, only positive or only negative poles will be obtained (unipolar plasters having only Northern poles or Southern poles, respectively) those magnetic sheets, which are produced in which positive and negative poles are alternatingly arranged, are preferred for the invention. Therefore, the arrangement of the poles is perpendicular to the plane of the sheet and skin. Said poles are present on the side facing the skin at distances of from 1 to 250 mm, preferably from 5 to 10 mm. The alternating assemblage of positive and negative poles has the special advantage that, thereby, not only larger areas of the body are exposed to therapeutical magnetic action, but also the optimum pole for the respective therapy is brought to the proximity of the optimum point. Namely, there has been found that certain diseases will more strongly respond to positive poles, while others will more strongly respond to negative poles. In the therapy employing these magnetic plasters according to the invention having both types of poles on the surface thereof, it is possible to make use of both types of poles and thereby to increase the chances of success. Furthermore, the magnetic fields of such magnetic plasters will more deeply penetrate into the organism, as they are crossed magnetic fields. Unipolar sheets carrying only positive poles have proven to be particularly successful in the treatment of disordered scars and keloids.

In the therapy using the magnetic plasters according to the invention, perceivable and measurable heat fields, which result in a considerable success of healing after only a few days, are generated, particularly of superficially extending pains and diseases. Patients, the therapy of whom by using the previously known therapeutical magnetic plasters with ferrite wafers showed no or only very little success, experienced alleviation or even healing after application of the magnetic plaster according to the invention for only a few days.

The flexible, permanently magnetizable plastic sheets, which are compatible with the skin and useful in the invention, may, for example, be of the rubber type of sheets that are used as the self-adhesive templates in labelling or painting automobiles. These sheets, while available with thicknesses of 0.5, 0.9, 1 and 1.5 mm, and have alternating positive and negative poles in strips 2 mm apart which is too close for the therapeutic purposes of the invention. For use in the invention, such sheets having a thickness of 0.5 mm have proven to be especially satisfactory, especially when the sheets have magnetic flux densities of about 0.04 T (400 Gauss) and in which positive and negative poles are alternatingly present having strip-shaped distances of 5 mm. There are basically suitable for the therapy such magnetic poles which possess from 0.005 to 1 T (50 to 10,000 Gauss). Particularly preferred are magnets having 0.04 to 0.20 T (400 to 2,000 Gauss). It is, however, preferred to produce and use sheets which are specifically adapted to suit the purpose of therapeutical application.

For attaching said sheets to the skin it is possible to either coat one surface of the sheet with an adhesive which is compatible with the skin, or to fix the sheet on the skin by aid of self-adhesive plasters which are compatible with the skin. Adhesives compatible with the skin are known in the art and are, for example, used in the production of conventional plasters. In so far as the magnetic plasters according to the invention are self-adhesive, a close contact between the sheet and the skin is ensured. This may involve some troubles at those locations of the body, which are susceptible to increased transpiring, even when the sheet has perforations or slits. It is, nevertheless, possible the fix magnetic sheets on the skin by the aid of self-adhesive plasters, particularly if sheets are used which are sensitive towards those solvents used for the application of adhesives that are compatible with the skin. It will basically suffice when the self-adhesive plaster will partially adhere to the magnetic sheet and partially adhere to the skin. As the magnetic sheets usually have a dark color, it may be advantageous to cover the magnetic sheet in total with a self-adhesive plaster and to fix it on the skin by means of projecting strips of the self-adhesive plaster. The attachment of the magnetic plaster according to the invention is optically less eye-catching because self-adhesive plasters may readily be skin-colored, all the more since a dark sheet will remain visible through lighter garments. It is recommended for self-adhesive magnetic plasters according to the invention, to cover the adhesive layer by siliconated paper. Said paper layer may be stripped off and disposed of prior to using the plaster on the body.

It is basically possible to laminate the reverse side of the self-adhesive magnetic plasters by an elastic skin-colored fabric layer in order to thereby render the plaster optically less perceptible. Besides, there is the possibility to coat, or to dye, the magnetic sheet on the side averted from the skin with a bright or metallic layer. Metallic coatings, moreover, have a reflecting property and thereby an enhancing effect. Comparative investigations, conducted with healthy persons, of the skin temperature and the change thereof as induced by the action of the magnetic plasters according to the invention and of conventional plasters with ingredients which stimulate the blood circulation, such as based on Extractum et Fructus Capsici, resulted in that no measurable increase in temperature is induced by the magnetic plasters according to the invention, whereas increases in temperature of 3° C. beneath the plaster and of 1° to 2° C. at a distance of up to 10 cm from the plaster are determinable with conventional therapeutical plasters having included plant extracts which stimulate the blood circulation. Thus, the increase in temperature as felt upon application of the therapeutical plasters according to the invention is subjective and is based on a change of the metabolism situation in the cells and in the surrounding connective tissues, whereas a certain artificial inflammation due to a higher blood circulation in the skin is generated by the conventional plasters with active ingredients.

Since both principles of action are entirely different, it is basically possible to combine these with each other. Therefore, a self-adhesive layer is chosen in one preferred embodiment of the magnetic plaster according to the invention, which layer additionally contains a substance which stimulates the blood circulation. These substances which stimulate the blood circulation may be any of those already known and with proven therapeutical effects. Substances from mustard, paprika, or Fructus Capsici, which stimulate the blood circulation, are particularly preferred. A mixture of Extractum et Fructus Capsici, amounting to about 0.05 to 5%, preferably from 0.1 to 3%, has proven to be valuable in conventional plasters and is, therefore, basically suitable to be incorporated in the same amount into the the self-adhesive layer of the magnetic plasters according to the invention.

As the magnetic plasters according the invention with the additive of a substance, which stimulates the blood circulation, exhibit two modes of action, a faster and more intensive effect will result from the application thereof.

Measurements of subcooled tissue with bad blood circulation led to the result that magnetic plasters according to the invention may effect measurable increases in temperature even without containing substances which stimulate the blood circulation.

Some embodiments of the magnetic plasters according to the invention are illustrated in greater detail by way of the following examples. It is, however, understood and will be self-evident to the artisan that further embodiments with different sizes and different materials will lead to corresponding results.

EXAMPLE 1

Magnetic rubber sheets having a thickness of 0.5 mm (supplier: Serimag, Leutschenbacher Str. 71, Zürich, Switzerland) and the dimensions of 125×100 mm were sticked to parts of body and skin, which showed severe rheumatic troubles, by means of a skin-colored self-adhesive plaster compatible with the skin. The patients felt a noticeable development of heat and an improved blood circulation of said parts of the body only a short time afterwards. The plaster was removed after 2 to 5 days. In some cases there was only observed a significant alleviation, while in other cases the pain had completely disappeared. In those cases in which only an alleviation had occurred, the therapy was repeated after 1 to 2 days, whereby a further alleviation was achieved.

EXAMPLE 2

A magnetic sheet according to example 1 was provided with holes 2 mm in diameter (i.e. perforated) at distances of 10 mm each and subsequently fixed in the same manner by means of a skin-colored self-adhesive plaster compatible with the skin. The skin area located beneath the plaster was less affected by sweat after the therapy, while the success of the therapy was not impaired.

EXAMPLE 3

A magnetic sheet according to example 1 was provided with slits having a length of 35 mm each at distances of 10 mm which were arranged in staggered positions to each other. The magnetic sheet had been coated on one surface with an adhesive compatible with the skin and had been covered with siliconated paper. The slits increased the elasticity of the plaster and, at the same time, allowed for a better transpiration. The success of the therapy was the same as observed in example 1.

An investigation of the magnetic sheet supplied by the firm of Serimag showed that the sheet comprised positive poles and negative poles in an alternating strip-shaped arrangement, the individual strips being at some distance to each other. The magnetic flux densities alternatingly amounted to plus and minus 0.04 T (400 Gauss). The sheets are compatible with the skin, exhibit rubber elasticity, and are so flexible that they engage to the parts of the body without any difficulties, and they do so even better when they have additionally been slit.

EXAMPLE 4

A magnetic sheet according to example 1 having the dimensions of 60×100 mm was provided with slits having a length of 15 mm each at distances of 15 mm, the slits being in staggered positions to each other. The magnetic sheet had been coated on one surface with an adhesive compatible with the skin, which adhesive contained 3% of Extractum et Fructus Capsici. The adhesive layer was covered with siliconated paper. The siliconated paper was readily peelable prior to the treatment, and sticking the plaster to desired areas of the body did not involve any problems. The slits increase the elasticity of the plaster and, at the same time, allow for a better transpiration. Addition of the substance that stimulates the blood circulation resulted in a subjectively as well as objectively increased development of heat in the covered areas which involves a greater and faster success of the therapy.

Typical embodiments of the magnetic plasters according to the invention are shown in FIGS. 1 to 4.

FIG. 1 shows a top plan view of a self-adhesive magnetic rubber sheet with alternating strips of (+) poles and (−) poles.

Figure 2:
FIG. 2 shows a cross-sectional view of the sheet of FIG. 1.

FIG. 2 shows a sectional view of the sheet of FIG. 1, with "a" denoting the adhesive layer and "b" denoting the magnetic sheet.

Figure 3:
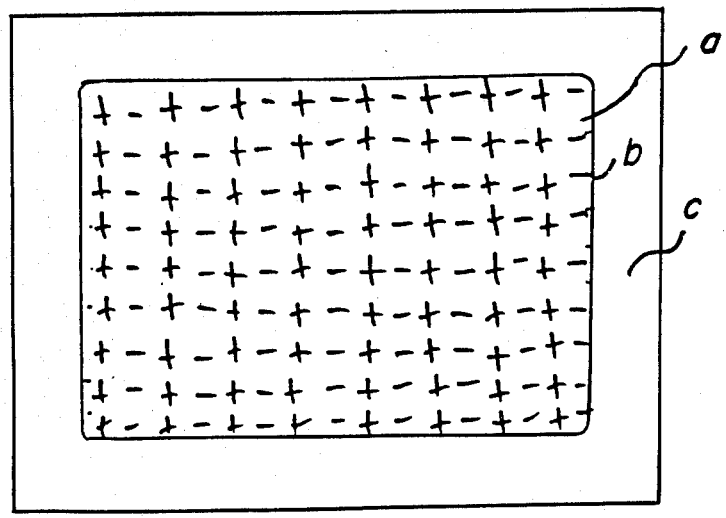
FIG. 3 shows a further embodiment in which the magnetic sheet is covered by a self-adhesive plaster.

FIG. 3 shows an embodiment, in which the magnetic sheet has completely been covered by a self-adhesive plaster; "a" denotes the self-adhesive layer of the plaster; "b" denotes the magnetic sheet, and "c" denotes the outer layer which is preferred to be skin-colored and which consists of a fabric or an elastic plastics material however, "c" can also be a foil layer, such as a gold foil.

Figure 4:
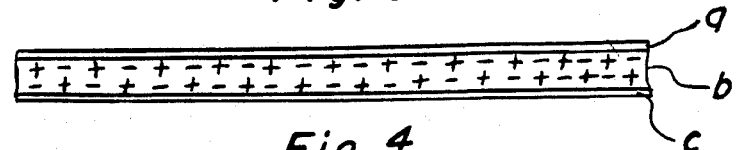
FIG. 4 is a partial cross-sectional view of the sheet of FIG. 3.

FIG. 4 is a partial cross sectional view of the sheet of FIG. 3.

The shown magnetic plasters may additionally be perforated or slit in the above-described manner. The indication of the magnetic poles (+) and (−) as shown in the Figures is understood to be exemplifying only. Depending on the respective purpose of application, there may be preferred to have exclusively (+) poles or exclusively (−) poles on the surface. While the exclusive presence of (+) poles on the skin will promote the healing, the exclusive presence of (−) poles will generate an artificial stimulation, similar to that caused by substances which stimulate the blood circulation.

EXAMPLES 5 THROUGH 8

Examples 1 through 4 were repeated using sheets which had specifically been produced for the purpose of therapeutical application. The sheets used were sheets having a thickness of 1 mm and alternating rows of (+) poles and (−) poles at distances of 4 mm, and 8 mm, respectively, which sheets were made by the firm of Yamauchi Rubber Industry Co., Ltd., Osaka, Japan. The magnetic flux density was about 0.06 T (600 Gauss). The results obtained with patients surpassed those of examples 1 through 4.

EXAMPLE 9

A sheet according to examples 5 through 8 was laminated on its reverse side with a thin gold-colored reflecting film and was processed to yield plasters. Said plasters showed an improved optical effect. The material was cut into strips having a width of 22 mm and a length of 1,000 mm, which strips were rolled up. When required, appropriate pieces were cut off and sticked to the skin.

I claim:

1. A flexible, permanently magnetized plastic sheet compatible with the skin having a flux density of about 50 to 2000 Gauss, a thickness of from 0.2 to 5 mm, and which sheet has alternating positive and negative parallel magnetized strips and the positive and negative poles of the strips are at distances between each other of from about 4 to 10 mm, said sheet being self adhesive to the skin or attachable to the skin by a self adhesive plaster compatible with the skin.

2. Magnetic sheet according to claim 1, characterized in that the sheet contains a self-adhesive layer which contains a substance which stimulates the circulation of the blood.

3. Magnetic sheet according to claim 2, characterized in that the substance which stimulates the circulation of the blood has been recovered from mustard, paprica or Fructus Capsici and is present in an amount of from 0.05 to 5 percent by weight of the self-adhesive layer.

4. Magnetic sheet according to any one of claims 1 to 3, characterized in that it has been perforated or slit.

5. Magnetic sheet according to any one of claims 1 to 3, characterized in that it has circular, oval, square or rectangular shape and its length and width are from 5 to 1,000 mm.

6. Magnetic sheet according to any one of claims 1 to 3, characterized in that the slits are present at distances of from 2 to 100 mm between each other, have a length of from 2 to 100 mm each, and are arranged in staggered positions to each other.

7. Magnetic sheet according to any one of claims 1 to 3, characterized in that it has holes present at distances of from 2 to 100 mm between each other and have a diameter of from 1 to 50 mm each.

8. Magnetic sheet according to any one of claims 1 to 3, characterized in that the plastics sheet consists of a material having rubber elasticity.

9. A magnetic plaster according to claim 1 in which the magnetized plastic sheet has a thickness of from 0.5 to 1.5 mm.

10. A magnetic plaster according to claim 1 which has a circular, oval, square or rectangular shape and its length and width are from 5 to 250 mm.

11. A flexible, permanently magnetized plastic sheet according to claim 1 having a fabric layer or a metallic layer on the sheet side which is to be out of contact with the skin.

12. A method of achieving magnetic therapy on a patient which comprises applying it to the skin area of the patient, where it is desired to produce a heat field for a therapeutic purpose, a flexible, permanently magnetized plastic sheet having a flux density of about 50 to 2000 Gauss, a thickness of from 0.2 to 5 mm, which sheet is compatible with the skin, and which sheet has alternating positive and negative parallel magnetized strips and the positive and negative poles of the strips are at distances between each other of from about 4 to 10 mm.

13. A method according to to claim 12 in which the magnetized plastic sheet contains perforations.

14. A method according to claim 12 in which the patient is a human.

15. A method according to claim 12 in which the plastic sheet has a fabric layer or a metallic layer on the sheet side away from the skin.

* * * * *

UNITED STATES PATENT AND TRADEMARK OFFICE
CERTIFICATE OF CORRECTION

PATENT NO. : 4,489,711
DATED : December 25, 1984
INVENTOR(S) : ARNO W. LATZKE

It is certified that error appears in the above-identified patent and that said Letters Patent is hereby corrected as shown below:

Page 1, column 1, item "[73]" before "Switzerland" insert --Wolfhalden--; column 3, line 7, delete "rubber"; line 8, before "sheets" insert --rubber--; line 37, change "the" to --to--; column 4, line 33, delete the second "the"; column 5, line 65, after "material" insert --;--; claims 9 and 10, line 1, change "plaster" to --sheet--.

Signed and Sealed this

Tenth Day of September 1985

[SEAL]

Attest:

DONALD J. QUIGG

Attesting Officer     Acting Commissioner of Patents and Trademarks - Designate

REEXAMINATION CERTIFICATE (3100th)
United States Patent [19]
Latzke

[11] B1 4,489,711
[45] Certificate Issued Jan. 14, 1997

[54] MAGNETIC PLASTER

[75] Inventor: Arno W. Latzke, Wolfhalden, Switzerland

[73] Assignee: Magnesystems, Inc., Los Angeles, Calif.

Reexamination Requests:
No. 90/003,497, Jul. 5, 1994
No. 90/003,591, Oct. 7, 1994
No. 90/003,617, Oct. 27, 1994

Reexamination Certificate for:
Patent No.: 4,489,711
Issued: Dec. 25, 1984
Appl. No.: 353,056
Filed: Mar. 1, 1982

[30] Foreign Application Priority Data

Oct. 2, 1981 [DE] Germany ............... 31 39 280
Dec. 3, 1981 [DE] Germany ............... 31 47 852

[51] Int. Cl.⁶ ........................................... A61N 1/40
[52] U.S. Cl. ................................................ 600/15
[58] Field of Search .................................. 600/9, 15

[56] References Cited

U.S. PATENT DOCUMENTS

3,483,494  12/1969  Cromie ........................ 335/303
3,546,643  12/1970  Virostek ....................... 335/303

FOREIGN PATENT DOCUMENTS

424257     9/1970   Australia .
1215110    4/1960   France .
2371916    6/1978   France .
56-7405    1/1981   Japan .
3600       of 1872  United Kingdom .

OTHER PUBLICATIONS

Hartwig, R. "Device for Generating an Magnetic Field at Parts of the Body", German Gebrauchmuster–Anmeldung (Utility Model Application No. 6904160, Feb. 1, 1969 (Translation provided from file of US 4489711).

*Electronics Engineers' Handbook*, Fink, D. G. et al. editors, 2d edition, McGraw–Hill Publ., New York, N.Y. ©1982, 1975 pp. 6–64–6–83.

*Primary Examiner*—Francis Jaworski

[57] ABSTRACT

Magnetic plasters are prepared from elastic magnetizable plastics sheets, which are either self-adhesive or may be fixed by means of self-adhesive plasters. They may optionally contain substances which stimulate the circulation of the blood in the self-adhesive layer.

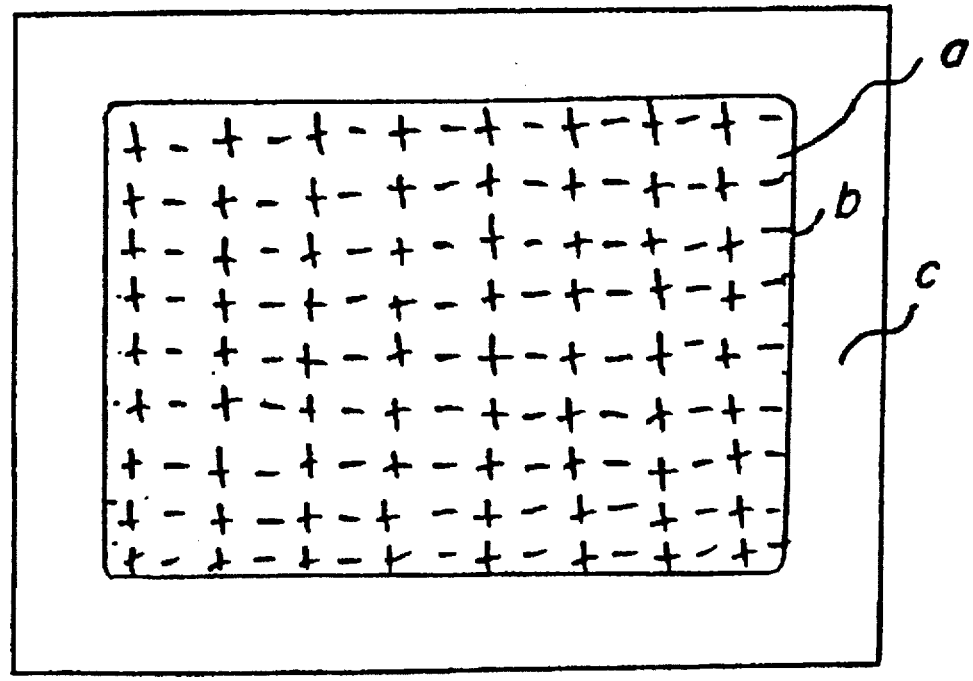

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1–15 is confirmed.

* * * * *